US006474165B1

(12) United States Patent
Harper et al.

(10) Patent No.: US 6,474,165 B1
(45) Date of Patent: Nov. 5, 2002

(54) MONITORING PIPES (75) Inventors: Mark Francis Lucien Harper, Cambridge (GB); Michael Ray Gorman, Cambridgeshire (GB)

(73) Assignees: Severn Trent Water Limited, Birmingham (GB); Thames Water Utilities Limited, Reading (GB); North West Water Limited, Warrington (GB)

( * ) Notice: Subject to any disclaimer, the term of this patent is extended or adjusted under 35 U.S.C. 154(b) by 0 days.

(21) Appl. No.: 09/555,947

(22) PCT Filed: Dec. 10, 1998

(86) PCT No.: PCT/GB98/03701
§ 371 (c)(1),
(2), (4) Date: Sep. 18, 2000

(87) PCT Pub. No.: WO99/31499
PCT Pub. Date: Jun. 24, 1999

(30) Foreign Application Priority Data

Dec. 12, 1997 (GB) .............................. 9726221

(51) Int. Cl.⁷ ...................... G01N 29/10; G01N 29/06; G01N 29/26
(52) U.S. Cl. .............................. 73/623; 73/625; 73/628
(58) Field of Search .................. 73/623, 622, 624, 73/625, 627, 628

(56) References Cited

U.S. PATENT DOCUMENTS 3,754,275 A * 8/1973 Carter et al. ................ 324/220
3,810,384 A * 5/1974 Evans ........................ 346/33 F
4,218,923 A * 8/1980 Triplett et al. ................ 73/623
4,404,853 A * 9/1983 Livingston ................... 73/622
4,856,337 A * 8/1989 Metala et al. ................ 324/220
5,063,780 A * 11/1991 Landry et al. ................ 702/39
5,431,053 A * 7/1995 Fink ........................... 73/596
5,454,267 A * 10/1995 Moreau et al. ............... 73/622
5,460,046 A * 10/1995 Maltby et al. ................ 73/623

FOREIGN PATENT DOCUMENTS

WO    WO 96/22527    * 7/1996

* cited by examiner

Primary Examiner—Hezron Williams
Assistant Examiner—Rose M. Miller
(74) Attorney, Agent, or Firm—Schweitzer Cornman Gross & Bondell LLP (57) ABSTRACT

An apparatus as disclosed for mounting a liquid-filled pipe by the use of ultrasound techniques. The apparatus comprises a vehicle capable of fitting inside the pipe, and of being transported along the pipe by the liquid flowing into it, together with rings of several ultrasonic transducers spaced circumferentially round the vehicle. The rings are so arranged that one ring operates in the reflection mode purely radially while two further rings operate as a pair in a longitudinal refraction mode. A fourth ring is used in a circumferential refraction/reflection mode. The vehicle has an associated power supply, data gathering and storage capability and a vehicle for measuring the distance traveled along the pipe.

21 Claims, 7 Drawing Sheets

MONITORING PIPES

This invention relates to monitoring pipes, and refers in particular to the use of ultrasonics to characterize liquid-filled pipes.

The owners of liquid-filled pipelines frequently wish to monitor the condition of those pipes. The uncertainties may include the material type, internal diameter, and thickness of the pipe, the material type, and thickness of any internal lining if present, the presence of corrosion on the internal surface of the pipe, the presence of corrosion on the external surface of the pipe, damage to the lining, the thickness of any deposits of material on the internal surface of the pipe or of the lining if present, the presence and extent of circumferential cracks, the presence and extent of longitudinal cracks, and the position of features such as bends, offtakes, valves and joints. In view of the high cost of replacing pipework, and the potential consequential damage due to fluid loss from a break in the pipework, it can be justifiable for the owner to carry out regular surveys of the condition of the pipework from within the pipe using a vehicle transported along inside the pipe. In some circumstances it is be important not to disturb any deposits on the pipe wall. In these cases the condition needs to be assessed without contacting the wall.

So-called 'intelligent pigs' are frequently used inside high-pressure gas pipelines to detect the presence of corrosion and other defects. The earliest vehicles were magnetic flux leakage devices. A powerful magnetic field is used to saturate the steel wall, and any defects in the pipe wall induce anomalies in the magnetic field downstream which are subsequently detected by the 'pig'. This device requires steel pipe with no internal lining, with no internal deposit, demands close contact with the wall, and has a high power requirement. Thus, it fails to match many of the requirements described above. Even in steel pipes the flux leakage method fails to detect longitudinal cracks very well. The magnetic flux leakage method has been applied successfully to fluid-filled unlined steel pipes, but the success was contingent upon the pipes being carefully cleaned of any deposit before the flux leakage device was used.

To detect longitudinal cracks, other vehicles inside high-pressure gas pipelines use ultrasonic transducers in shear mode. Fluid-filled resin wheels are pressed closely against the wall of the pipe, and used to couple ultrasonic shear waves into the wall. Ultrasonic waves in this instance refer to elastic waves at high frequencies in the hundreds of kilohertz (and even low megahertz) ranges. A compression wave is analogous to the visible motion transmitted along a stationary line of railway wagons when struck by a heavy diesel locomotive. A shear wave is analogous to the manner in which a side-winder snake manages to make forward progress by wriggling its body. The shear waves induced by the fluid-filled resin wheels travel circumferentially around the pipe, and are detected by adjacent wheels. In principle this technique can detect longitudinal cracks. It is evident though, that in many respects the method fails to address the full problem of condition monitoring described above. The fluid-filled wheels are required inside the gas pipe because the high impedance mismatch between gas and solid result in a near total reflection at the inner surface of the pipe if the waves were launched in the gas. This limitation does not apply in liquid-filled pipes for compressive waves. The liquid can provide a good coupling between compressive waves in the liquid and in the solid.

In the oil industry, ultrasonics have been used in reflection mode as caliper tools to measure the diameter of wells deep underground. Such wells are generally filled with liquids of various types. A tool inserted into the well projects an ultrasonic compression pulse radially through the liquid, and measures the time take for the first reflection to return from the wall. After the well has been drilled it is usually lined with a steel casing to keep it open. Cement is injected behind the casing into the space between the casing and the rock as drilled. An ultrasonic tool is sometimes used in cased wells to check the bond between the casing and the cement. An ultrasonic pulse penetrates through the steel casing, through the cement, and into the rock. The quality of reflection from the casing-to-cement interface is a measure of the quality of the cement bond to the casing. A good bond gives a lower-magnitude reflected pulse than the situation where a fluid-filled micro-annulus has developed between the casing and the cement. Another oil industry tool uses ultrasonic waves in refraction mode. An ultrasonic pulse is projected at an angle to the steel wall, and it couples by refraction into the casing and into the rock behind the casing. The transmitted pulse is detected by a receiver also at an angle to the wall, so a second refraction is required to detect the transmitted signal. The presence of a micro-annulus indicating a poor cement bond prevents good transmission into the rock, and this gives a received signal which differs from that which obtains when the bond is a good one.

Another method used inside steel pipes is commonly referred to as remote-field eddy current. An induction coil creates a magnetic field axially along the pipe whose return path is partly along the pipe wall and partly along the surrounding medium. The flux normal to the pipe wall is measured by probes close to the wall. Defects cause measurable disturbances in that flux. The method cannot be used in non-magnetic pipe, and gives no information about lining or deposits. As with magnetic flux-leakage devices, this device requires the wall inner surface to be cleaned of any deposits before being used.

Ultrasonic methods are used inside pipes in a reflection mode to determine pipe diameters and to detect the presence of a micro-annulus in cement surrounding the pipewall. They are also used in refraction mode to detect the presence of a micro-annulus in cement surrounding the pipewall. They have also been used in both reflection and refraction modes to detect flaws in pipes. However, in all these cases the material of the wall is assumed to be known so that the speed of sound in the wall material is known. And in none of the above cases is there presumed to be any lining or deposit on the inner surface of the wall. This invention sets out to combine ultrasonic methods in reflection, refraction and reflection-refraction modes so as to identify the materials of the pipewall, the lining and any interior debris prior to using this information to size the pipewall, radius and thickness, the lining and any debris and then to identify features such as cracks, corrosion and fittings.

The invention proposes for this purpose Apparatus for the characterization of a liquid—filled pipe, which Apparatus comprises:
1. a vehicle capable of fitting inside the pipe and of being transported by the liquid along the pipe.
2. the vehicle carrying rings of several ultrasonic transducers, preferably disposed at equidistance circumferentially around the ring and the rings arranged such that:
   2.1 one ring of transducers operates in the reflection mode purely radially.
   2.2 two rings of transducers operate as a pair displaced axially to each other. The pair is used in a longitudinal refraction mode. One ring of transducers emits pulses along the pipe at the critical angle to the wall such that the wave is refracted as waves travelling within the debris, lining and pipewall, and the refracted wave is received by the other ring of transducers.

2.3 the emit ring of transducers of the refraction mode pair also has the capability of receiving reflected echoes, this being a refraction/reflection mode.

2.4 one ring of transducers is used in a circumferential refraction/reflection mode. Each transducer emits pulses in a radial plane but at the critical angle circumferentially to the wall such that the wave is refracted as a circumferential wave along the debris, lining and pipewall and the transducer receives reflections back along the same path.

3. the vehicle carrying power to supply the ultrasonics and associated data gathering and data storage.

4. the vehicle carrying data storage capacity to save the ultrasonic information which is captured at regular intervals of distance along the pipe.

5. the vehicle optionally carrying an umbilical cable transmitting power and incorporating a data communication link back to the pipe inlet to avoid power and memory storage being required on board.

6. the vehicle carrying a means of measuring the distance travelled along the pipe.

In one aspect, therefore, the invention provides apparatus for use in the characterization of a liquid-filled pipe, which apparatus comprises a vehicle capable of fitting inside the pipe and of being transported by the liquid along the pipe, the vehicle carrying rings of several ultrasonic transducers arranged such that during utilisation the rings are co-axial with the pipe and spaced along the vehicle, and such that a first ring of transducers operates in the reflection mode purely radially while a second and a third ring of transducers operate as a pair displaced axially to each other, the pair being used in a longitudinal refraction mode in which one ring of the pair emits pulses along the pipe generally at the critical angle to the wall—that is to say, along directions spread in a cone so as to accommodate expected variations in the critical angle of the pipe, liner and debris materials—such that the wave is refracted as waves travelling within the debris, lining and pipe wall, and the other ring receives the refracted wave, the emit ring of transducers of the refraction mode pair also has the capability of receiving reflected echoes, this being a refraction/reflection mode, and a fourth ring of transducers is used in a circumferential refraction/reflection mode in which each transducer emits pulses in a radial plane but at the critical angle circumferentially to the wall such that the wave is refracted as a circumferential wave along the debris, lining and pipe wall and the ring then receives reflections back along the same path, the vehicle also carrying means for measuring the distance travelled along the pipe.

In a second respect the invention provides a Method of characterizing a pipe filled with moving liquid, in which Method:

1. the pipe characterizing Apparatus as described above is transported along the pipe by the liquid within the pipe.

2. the distance travelled by the Apparatus is measured by one means or another.

3. ultrasonic pulses are used in radial reflection, in longitudinal refraction, in longitudinal refraction/reflection and in circumferential refraction/reflection modes at regular intervals of distance along the pipe and the received ultrasonic information is stored.

4. the ultrasonic data is processed to determine the materials of the pipewall, the lining of the pipe, the debris accreted on the inside of the pipe, the radius of the pipe, the thickness of the pipewall, the lining and the debris, to detect circumferential and longitudinal cracks, damage to the lining and corrosion of the pipewall interior and exterior, and to locate fittings such as joints, valves and junctions.

5. the preferred option is to display processed information as a function of distance along the pipe.

The preferred form of the vehicle is an autonomous device having on-board sufficient power and memory for examination of long distances exceeding one kilometer along the pipe. The vehicle consists of separate modules small enough to enter the pipe by means of suitable fittings. In the water industry existing fittings for entry and removal would be fire hydrants from which the whole top assembly can be removed. If no suitable entry points exist then the vehicle is inserted and recovered by means of custom-made under-pressure live-launch and recovery stations that are fitted onto the pipe when required.

The modules connect together mechanically and the connection includes power and data transmission between modules. The leading module has some means such as a collapsable drogue to ensure the flow of liquid provides sufficient drag to produce forward propulsion for the string of modules. The modules are designed to be neutrally buoyant to minimize contact with the pipewall. As well as being neutrally buoyant, the centre of gravity of each of the modules is below the geometrical centre of the module. This ensures that on average the module will remain the same way up and so reduces the requirement for any form of measurement of vertical alignment. On some modules, such as the ultrasonic modules, it is helpful to have light springs pressing gently against the wall. Centralizing the ultrasonic modules reduces the processing required to extract information from the ultrasonic data.

Ultrasonic measurements are made within the pipe at regular intervals and the results are presented as a function of distance travelled along the pipe. This distance travelled can be measured by means of a wall-contacting wheel but the preferred method uses acoustic means to measure the distance. The vehicle emits an acoustic pulse at regular intervals which is detected at both ends of the pipe. At launch, the time for the signal to reach the far end of the pipe, $t_0$, multiplied by the speed of sound in the liquid, $V_f$, gives the length of the pipe $L = v_f t_0$. During transport, the difference, $\Delta t$. between time of arrival of the pulse at the launch end of the pipe and the time of arrival of the pulse at the recovery end of the pipe gives the distance, x, of the vehicle from the launch end as $x = \frac{1}{2}(L + v_f \Delta t)$. A single ended alternative to this method is to transmit an acoustic signal from one end of the pipe and have a transponder on the vehicle that emits its own acoustic reply when it detects the arrival of the first transmitted signal. At the transmission end of the pipe, the time between emitting a signal and receiving the second one back multiplied by the speed of sound in the liquid gives the distance to the vehicle. The transmission and response signals have to be of different character so as to distinguish the transponder response signal from any reflections of the original transmission signal. If an inertial navigation system (INS) is fitted to the vehicle then the distance travelled can be deduced from the INS. Even if such a system were available, the preferred method would also include acoustic means of measuring distance as backup data.

The combination of ultrasonic transducers is transported axially along the inside of a pipe by the vehicle on which they are mounted while measuring in radial reflection mode, in axial refraction mode operating at an angle to the wall, in axial refraction-reflection mode operating at an angle to the wall and in circumferential refraction-reflection mode operating at an angle to the wall such that this complete set may be used to determine the velocity of ultrasonic waves in the pipewall, the internal diameter of the pipe, the pipe thickness, the velocity of ultrasonic waves in any lining if present, the thickness of any internal lining, the presence of corrosion on the internal surface of the pipe, the presence of corrosion on the external surface of the pipe, damage to the lining, the thickness of any deposits of material on the internal surface of the pipe or of the lining if present, the presence and extent of circumferential cracks, the presence and extent of longitudinal cracks and the position of features such as bends, offtakes, valves and joints.

A wide variety of pipes can by examined by the ultrasonic Method, including, among other materials, cast-iron, ductile iron, steel polyethylene, PVC, and asbestos-cement. The pipes sizes that can be examined by an autonomous vehicle range from 150 millimeters nominal bore to of the order of one meter in diameter. The pipewall thickness will vary according to the liquid, the pressure in the liquid, the flowrate anticipated, the material of the pipewall, the structural support for the pipe and its design lifetime. Typical thicknesses range from a few millimeters to a few centimeters. The linings of pipes depend upon the material of the pipewall and the liquid inside and are not always used. Typical materials for linings include cement mortar, bituminous layers, epoxy layers and various plastics. Whether or not there is any accretion to the inside of the pipe, or debris, depends upon the liquid used and the flowrate involved. In the water industry typical accretions consist of so-called tubercular growths of hard material initiated by algae at the wall or calcareous deposits. In the petroleum industry typical accretions tend to be a waxy form of hydrocarbon. Very often the material of the pipewall, the lining and any accretion is not known beforehand. In this invention it is refraction mode measurements, in identifying the various materials by determining the speed of sound, which allow reflection mode measurements to determine radii and thicknesses of materials. The further combination of all modes of measurement allows for identification of corrosion, longitudinal cracks, circumferential cracks and fittings such as valves, joints and junctions.

The number of ultrasonic transducers used determines the circumferential resolution of the measurements. For instance, in reflection mode a ring of eight transducers used inside a 150 mm bore pipe gives a circumferential resolution of 59 mm. The same circumferential resolution applies to a pair of rings of transducers used in refraction mode, and to a ring used in longitudinal refraction/reflection mode and to a ring used in circumferential refraction/reflection mode. The invention describes the Method of carrying out the above measurements, namely with ultrasonics in reflection, refraction and refraction-reflection modes, while transporting the set of measurement transducers axially along the inside of the pipe. The speed of ultrasonic waves in the solid and liquid is high. For example typical speeds of sound in iron and in water are 5000 m/s and 1500 m/s respectively. These are sufficiently high compared with the speed with which the transducers can be translated axially along a pipe by an autonomous vehicle, typically of order 1 m/s or less, that measurements may be taken to vary continuously with distance along the pipe. All the measurements are taken on a repeated basis as the transducers are transported along the pipe. The rate of repetition of the measurements compared with the rate of translation along the pipe determines the axial resolution of the measurements.

For example, if the axial translation rate of the module bearing the ultrasonic transducers was 0.1 m/s then a repetition rate of ten times per second gives a longitudinal resolution of 10 mm. Ultrasonic transducers for both emit and receive are of piezo-electric type such as marketed by Morgan Matroc Limited of Transducer Products Division, Thornhill, Southampton, Hampshire S019 7TG. There are typically eight or more equally disposed in a ring around the body of the transporting module in any one transverse plane. One such ring is used for reflection mode measurements. A pair of rings axially displaced relatively to each other are used for refraction and refraction-reflection mode measurements along the pipe. A further ring is used for refraction measurements circumferentially around the pipe.

Specific embodiments of the invention are now be described by way of example with reference to the accompanying drawings, 1, 2, 2a, 3, 4, 5 and 6 in which.

Figure 2:
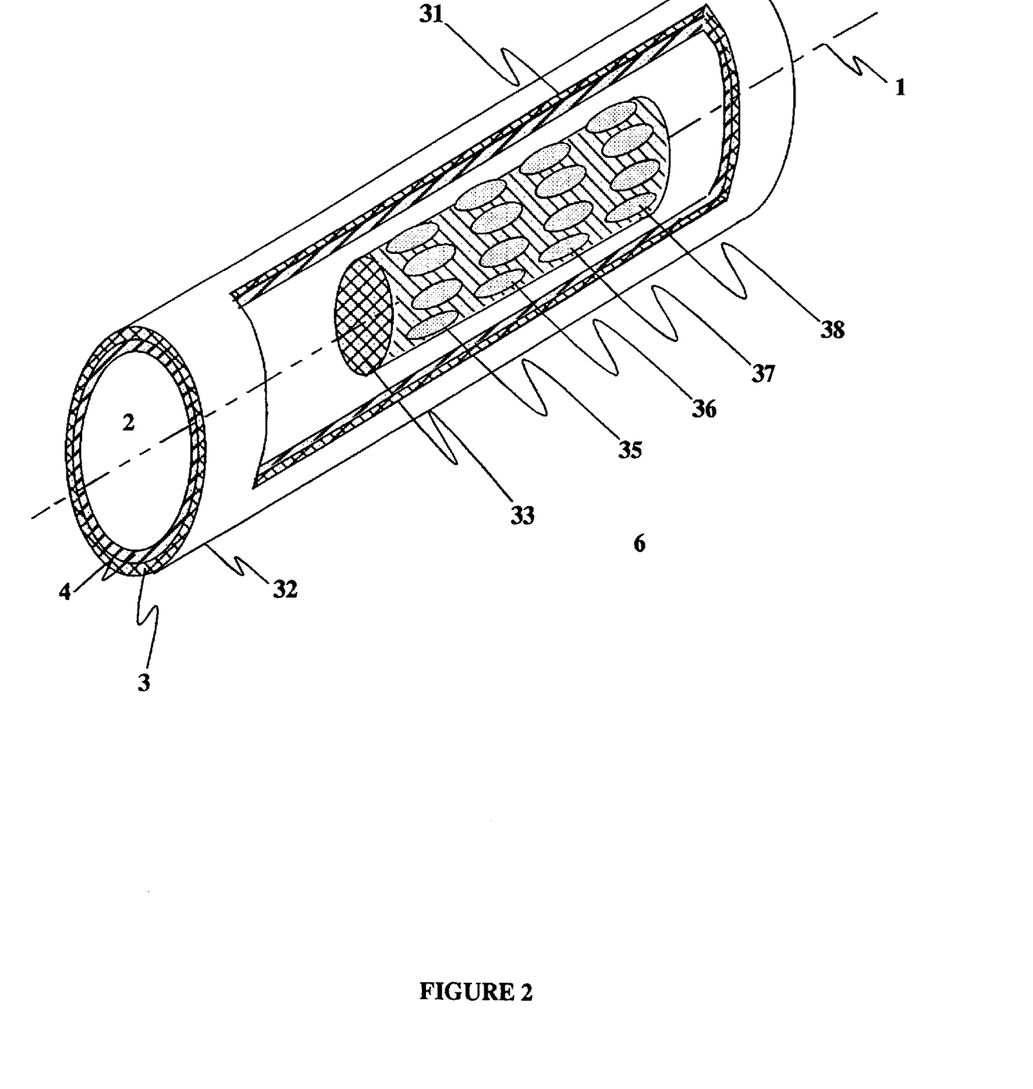
FIG. 2 shows a schematic view of a pipe with a cut-away section showing a vehicle inside with four rings of ultrasonic transducers around the periphery.
Figure 2A:
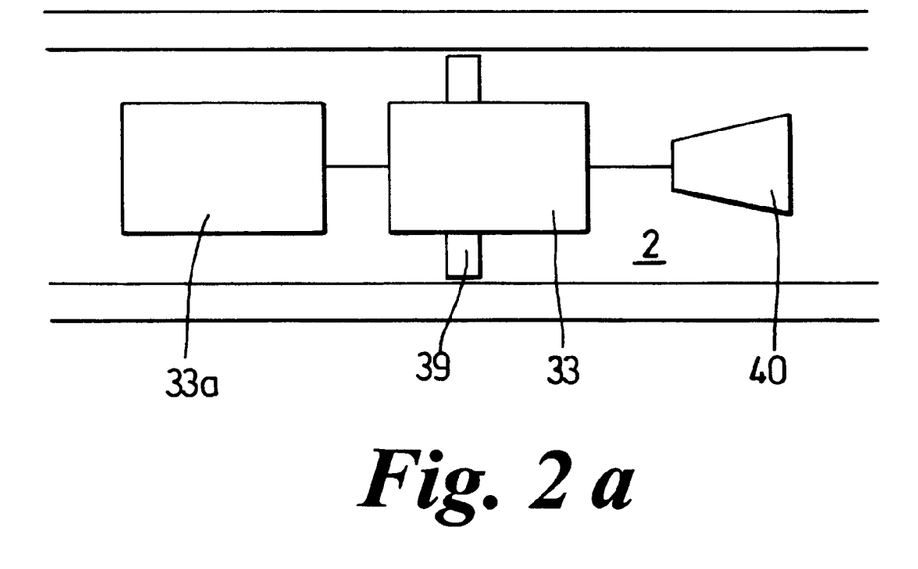
FIG. 2a is a simplified schematic sectional view of a pipe illustrating a multiple-module vehicle inside supported by spacer means and utilizing a collapsible drogue.
Figure 3:
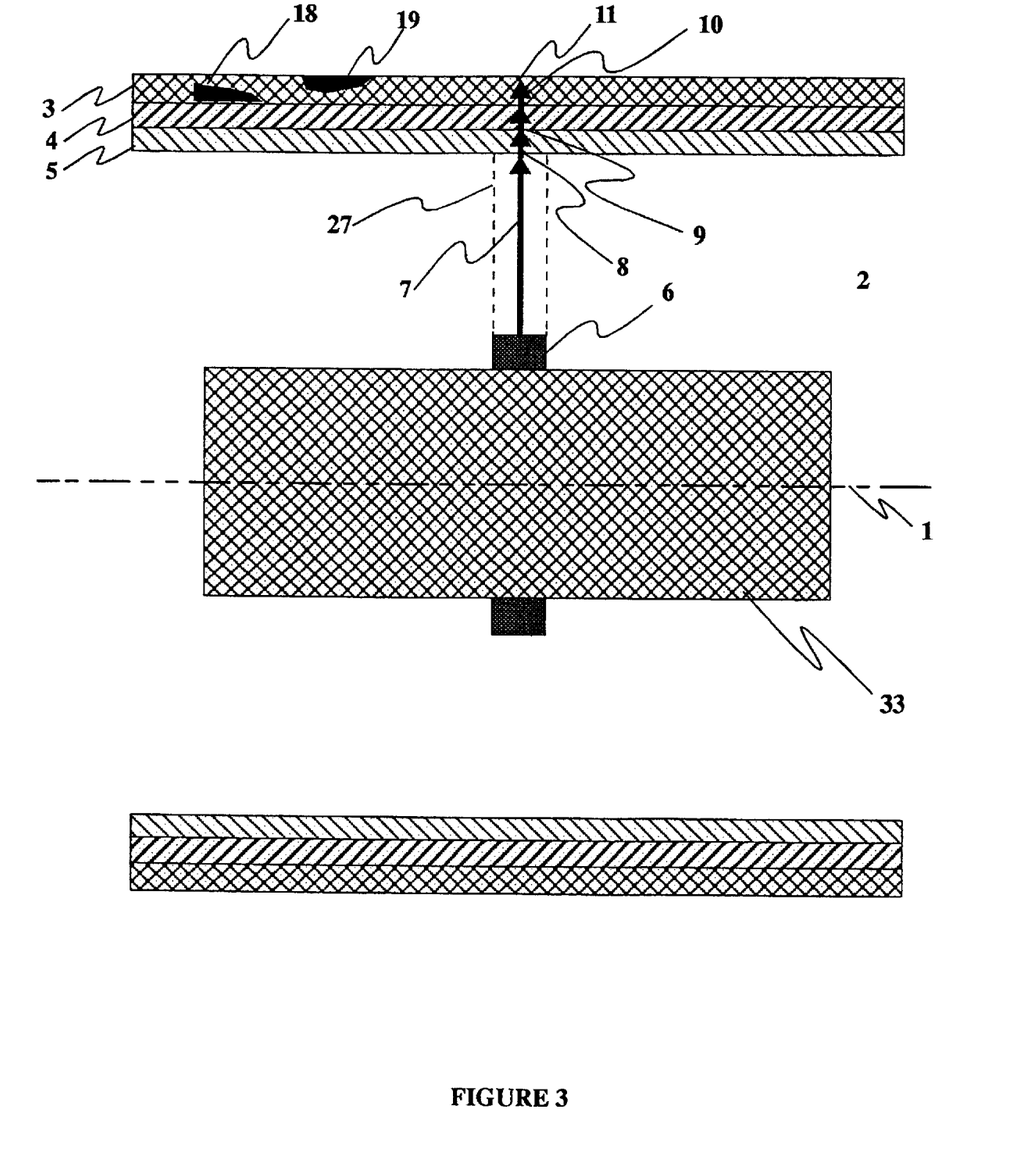
FIG. 3 shows a longitudinal (along its length) cross-section through a pipe with an ultrasonic transducer emitting and receiving waves radially.

FIG. 2 shows a schematic view of a pipe 32 filled with liquid 2 with a cut-away section 31 showing a module 33 inside with four rings of ultrasonic transducers around the periphery. One pair of rings consist of a ring 35 for transmission and ring 38 for reception of longitudinal refraction mode waves. The transmission ring 35 also serves to receive longitudinal refraction/reflection mode waves. Ring 36 is used for radial reflection mode waves. Ring 37 is used for circumferential refraction/reflection mode waves. The vehicle serves to transport the arrangement of transducers along the pipe. The module 33, which may form part of a chain of such modules 33, 33a (FIG. 2a), is free floating In the pipe. It is centralized by spacer means 39, preferably in the form of springs which press gently against the pipe wall. The modules are drawn along by the drag of the flow of liquid 2 upon a collapsible drogue 40. The other modules 33a have various functions such as power supply and memory storage. The modules are small enough to enter the pipe by means of suitable fittings. The cross-section through the pipe 32 shows the pipe wall 3 and internal lining 4. The debris on the lining is not shown. FIG. 3 shows an axial cross-section through a pipe with centerline 1 containing liquid 2 and showing on one side of centerline 1 the pipe wall 3, lining 4 to the pipe wall 3, and deposit 5 on the lining 4. An ultrasonic transducer 6 mounted on the module 33 is shown emitting a pulse which is transmitted 7 through the liquid and reflects at the interface 8 with the deposit 5, at the interface 9 with the lining 4, at the front face 10 of the pipe wall 3, and at the back face 11 of the pipe wall 3. The width of the pulse need not extend greatly beyond the size of the transducer 6. (The width is shown delimited by the parallel lines 27.) These reflections travel back along the same route to the transducer 6 at which they are detected. Within any of these materials there may be multiple reflections.

The timing of return of the reflected pulses indicates the thickness of the deposit 5, of the lining 4, of the pipewall 3 and the distance of the transducer 6 from the wall. The transducer is at a known distance from the centreline of the pipe 1, and so the radius of the pipe is determined as long as the speed of sound in the solid materials is known. The liquid material must have a known consistent speed of sound.

A defect 18 is shown on the outside of the pipewall 3, and a second defect 19 is shown on the inside of the pipewall 3. The timing of the return reflections from such defects gives a measure of the depth of the defects. The same applies within the lining.

In FIG. 3 the transmitted wave 7 is shown without any lateral spread 27 because there is no need to include significant lateral spread beyond the width of the emitting transducer 6, although there will inevitably be some spread by diffraction.

Figure 4:
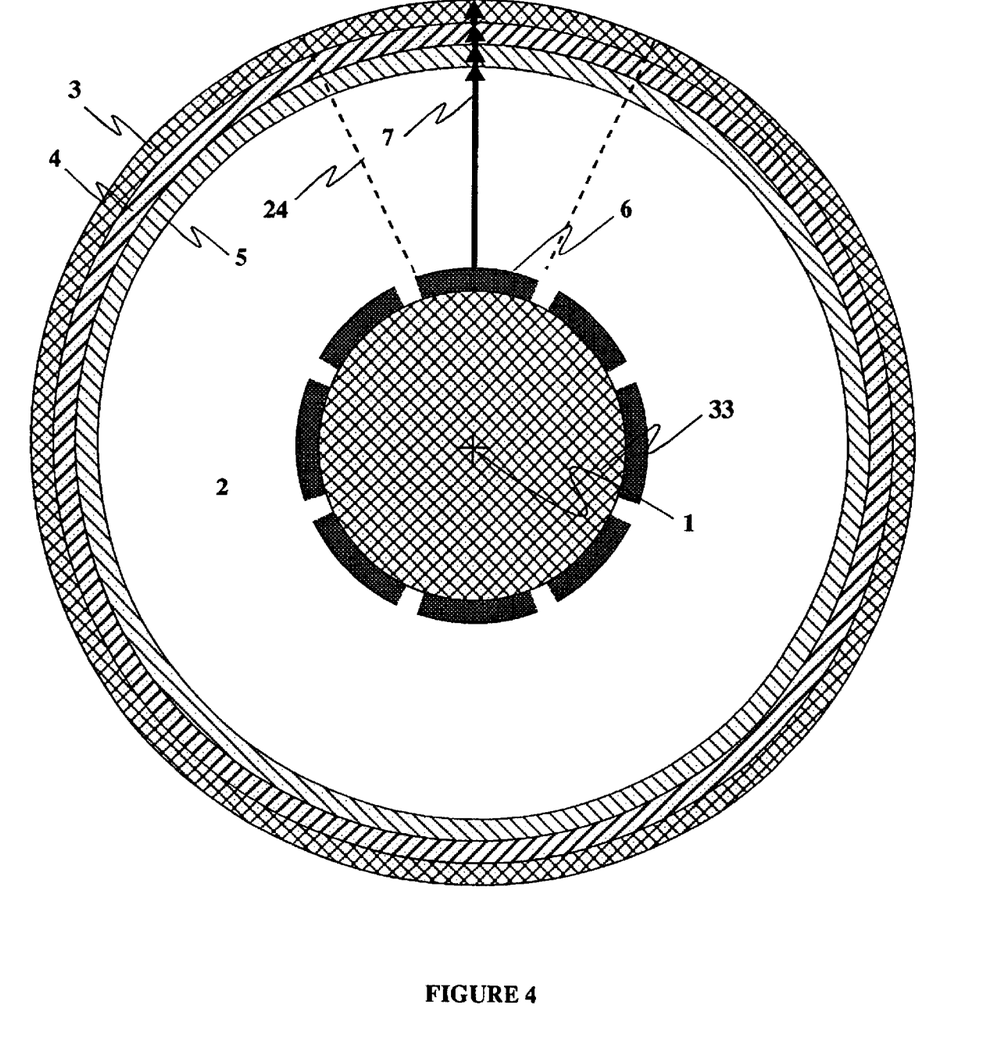
FIG. 4 shows a transverse cross-section through the pipe with an ultrasonic transducer emitting and receiving waves radially.
Figure 5:
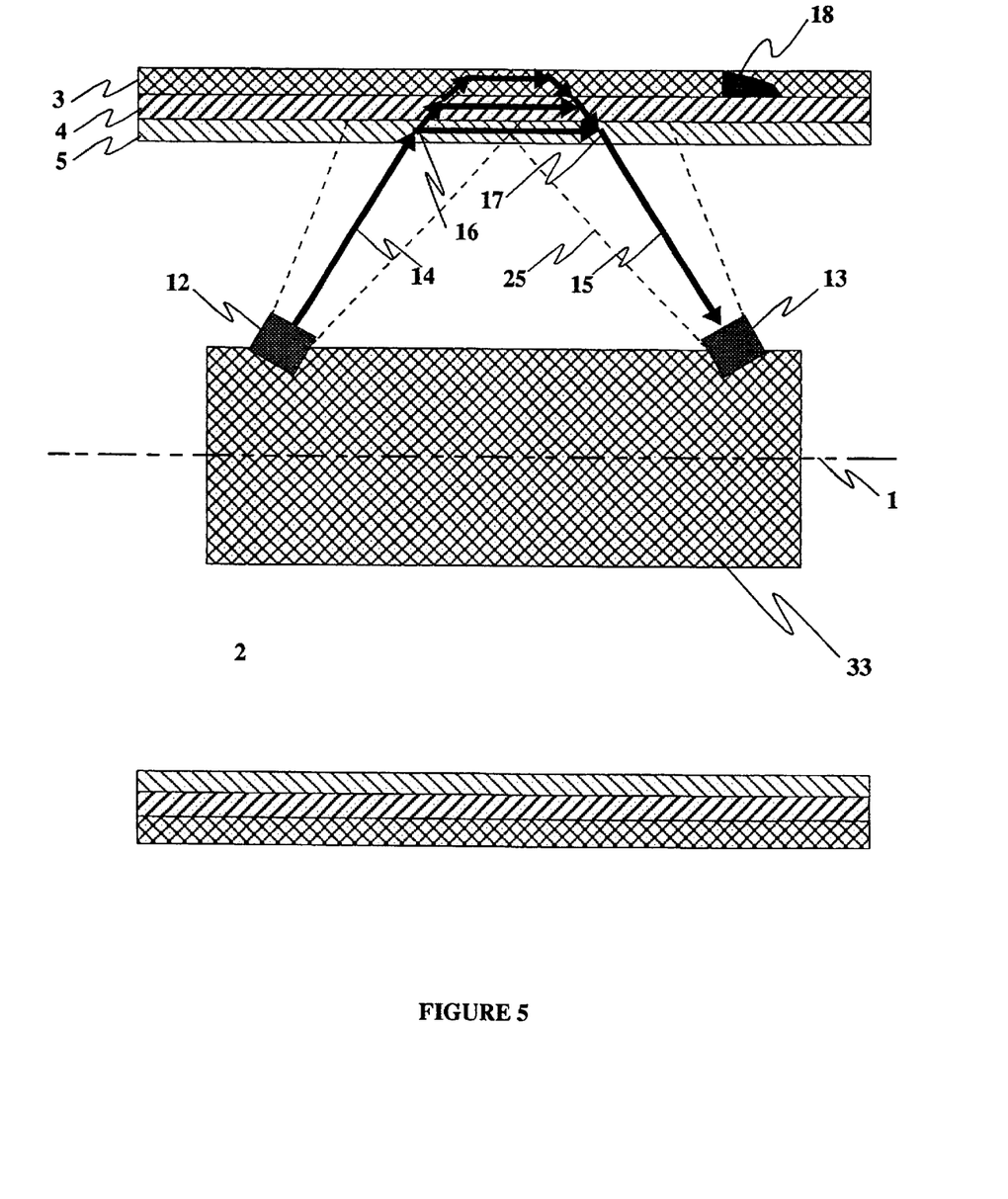
FIG. 5 shows a longitudinal (along its length) cross-section through a pipe, with one ultrasonic transducer emitting waves at an angle to the longitudinal axis of the pipe and a second transducer receiving the refracted waves at a position displaced axially from the emitter.

In FIG. 4 is shown a radial cross-section through the same arrangement of reflection mode transducers 6. Each of eight transducers 6 is shown lying on a circle about centreline 1. The transmitted wave 7 is shown to extend over an arc delimited by the dashed lines 24 determined by the size of the transducer 6. The resulting measurements based on reflections are an average echo received from the surface area delimited by the arc 24 and this arc determines the angular resolution. In FIG. 5 is shown an axial cross-section through the pipewall 3 with an ultrasonic transducer 12 transmitting a wave 14 at an angle to the wall, shown with a deposit 5 on a lining 4. The wave 14 is refracted into the various materials at the critical angle 16, travels along the materials, and refracts out again at the same critical angle 17, and the wave 15 is received at a second transducer 13 displaced axially from the first one 12 from which the wave was emitted. The critical angle 16 depends upon the material, and so the waves 14 are deliberately spread in a cone shown by dashed lines 25 to accommodate variations expected in angle 16. A circumferential defect 18 is shown, and this could represent a crack, corrosion, or a fitting such as a flange, valve or joint to a side-branch pipe. The travel time through the different materials indicates the speed of sound in those materials. The speed of sound in the materials identifies the materials of the pipewall, the lining and the debris. In addition, the speed of sound in each material is needed to multiply the transit times of reflection mode radial pulses so as to convert these times into absolute distances including thickness of debris, thickness of lining and thickness of pipewall. The transmitted wave 14 is reflected at a defect 18 when the defect lies between the transducers 12 and 13, and the reflected wave is received at the same transducer 12 as emitted the original pulse. Reflections from the defect 18 indicate the presence of such defects.

Figure 6:
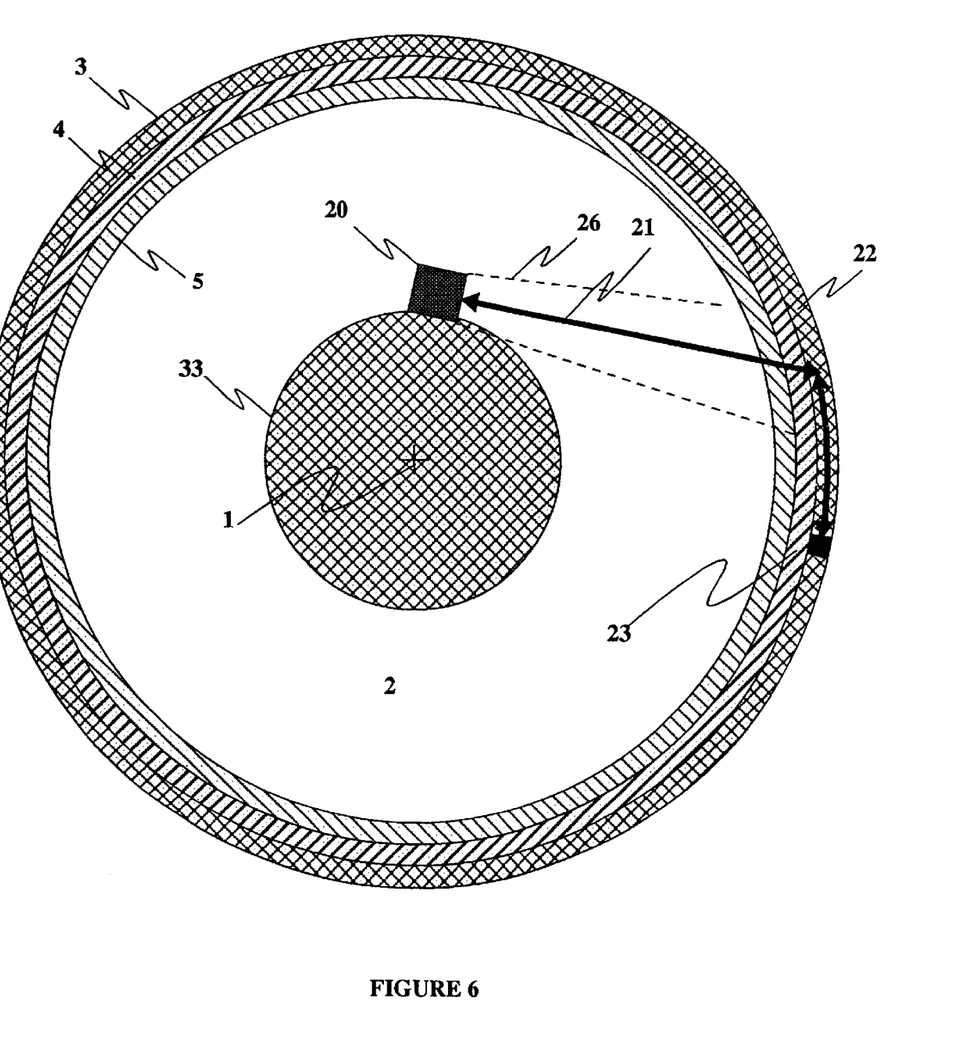
FIG. 6 shows a transverse cross-section through a pipe with an ultrasonic transducer emitting waves at an angle to the pipe in the circumferential plane. The waves are being reflected by a defect in the pipe and then received by the same transducer as emits the pulse.

FIG. 6 shows a radial cross-section through the pipe with a transducer 20 emitting a wave 21 at the critical angle to the wall such that the wave travels circumferentially around the pipewall 3 within the wall material. A longitudinal defect reflects the wave back to the emitting transducer 20, and the timing of the return indicate the position of the defect. To accommodate variations in critical angle, the wave 21 extends across a cone delimited in FIG. 6 by a dashed line 26.

In reflection mode, a pulse is emitted by the ultrasonic transducer in a radial direction, normal to the pipe wall, and the reflections from surfaces normal to the path of the ultrasonic wave are received, commonly at the same ultrasonic transducer. Surfaces normal to the path of this reflection mode pulse could be the inner surface of any deposit and the interfaces between deposits, lining, corrosion and the pipewall itself at inner and outer surfaces.

The timing of radial reflection mode signals gives an indication of the radial dimensions of the pipe, thickness of the pipewall, pipe lining and deposits. Suppose, for example, that the speed of sound in the liquid is $v_f$ and the first pulse reflection is received after $t_f$ seconds. Then the distance travelled through the liquid from the transducer to the innermost face of the wall, possibly the debris, and back to the transducer is the product $0.5 v_f t_f$. The next reflection is from the interface between the debris and the lining. If this reflection is received at time $t_d$ and the speed of sound in the debris was $v_d$ then the thickness of the debris is the product $0.5(t_d - t_f) v_d$. The same principle is applied to any number of reflections provided that it is possible to distinguish them. Any anomalies in timing indicate the presence of various defects. For example, if measurements continuously yield the thickness of the pipewall as the transducers travel axially along the pipe and then at some point there is a much reduced time of arrival from the outside face of the pipewall, this indicates that there is substantial corrosion at that point on the wall. There may be multiple reflections within any of the materials in the path and most likely within the pipewall. Such multiple reflections result in repeated echoes at the receiver and serve to reinforce the calculation of material thickness. The time between these multiple echoes multiplied by the speed of sound in the material yields repeated estimates of the thickness of the material.

Timing information gives the radial distance from the transducer to the first reflecting face, such as the debris, since the speed of sound in the liquid is known. However the timing information cannot give the dimensions of the materials, debris, lining or pipewall, unless the speed of sound in these material is known accurately. The speed of sound in the materials comes from timing of the pulses transmitted by the refraction mode pulse, described next.

Figure 1:
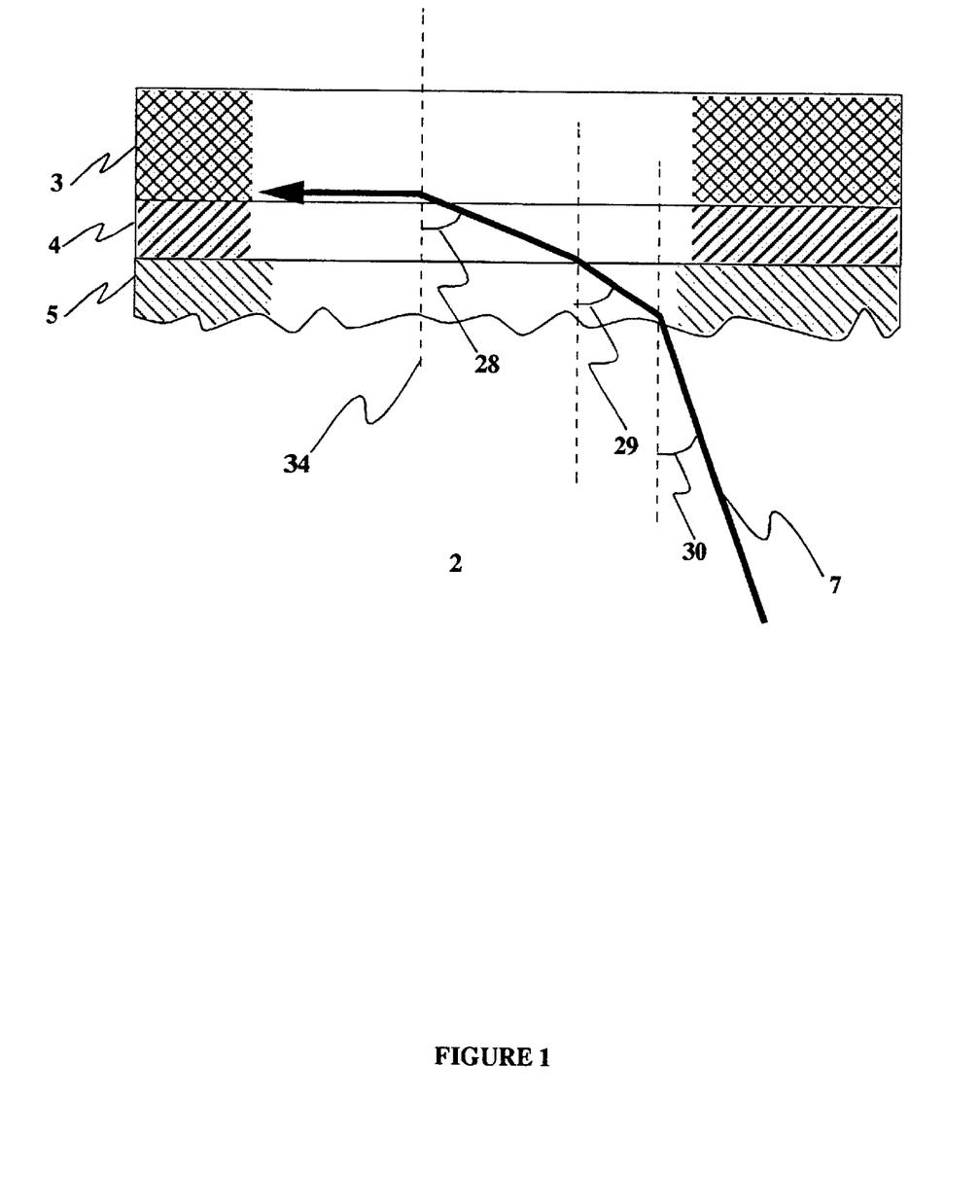
FIG. 1 is an explanatory sketch concerning Snell's law of refraction.

In refraction mode, a pulse is emitted by the ultrasonic transducer at an angle to the pipe wall known as the angle of incidence. The angle involved is determined by Snell's law which matches the speed of sound in two media by the sine of the angles subtended to the normal at the interface by the waves in the two materials. In FIG. 1 for example, a wave 7 is shown being transmitted from liquid 2 into debris 5 at an angle of incidence 30 to the radial normal 34, from debris into the lining at an angle 29, from lining into pipewall at an angle 28. If the speed of sound in liquid, debris, lining and pipewall is represented by $V_f$, $V_d$, $v_l$, and $v_p$ respectively and the angles 30, 29, 28 are represented by $\alpha_f$, $\alpha_d$, and $\alpha_l$, respectively then $$\sin \alpha_f = \frac{v_f}{v_p}, \qquad \sin \alpha_d = \frac{v_d}{v_p}, \quad \text{and} \quad \sin \alpha_l = \frac{v_l}{v_p}.$$

The wave is refracted into the pipe wall and travels along the wall. The angle of incidence of the wave with the pipe that results in a wave within the pipewall travelling parallel to the pipewall is referred to as the critical angle for refraction into the pipewall. The critical angle for refraction into the lining will be slightly greater and the critical angle for refraction into the debris will be slightly greater still. By transmitting waves over a small range of angles, all the critical angles are included. At angles of incidence greater than the critical angle the waves totally reflect at the interface. At angles of incidence less than critical the introduction of longitudinal waves into the pipewall is less efficient. The plane containing the normal to the pipewall and the projected wave can be longitudinal, in which case the direction of travel through the solid is longitudinal (axial) down the pipe. Alternatively, the plane containing the normal to the pipewall and the projected wave can be transverse to the pipe in which case the direction of travel in the solid is circumferential. As the pulse travels along it is continuously refracting out again from the wall, back into the liquid region, and some of these refracted transmission waves are detected at a second, receive, ultrasonic transducer. The refracted waves can also meet areas of reflection along the pipewall, such as cracks, corrosion and joints, and the reflected waves are detected at the same transducer from which the wave was emitted.

The first arrival at the receive transducer in the refraction mode is that of waves transmitted through the pipewall since that material has the highest speed of sound, around 500 m/s. The length of the paths in the refraction mode are determined by the distance apart of the emit and receive transducers and this is prescribed a-priori by the geometry. Since the speed of sound in the liquid can be presumed to be known, the time of the first arrival pulse yields the speed of sound in the pipewall. Suppose the distance from the transducer to the debris is $x_f$, the thickness of debris is $X_d$, thickness of lining is $x_l$, the distance between emit and receive transducers is L and the time to receive the pulse is t then we have for the speed of sound in the pipewall the expression $$v_p = \frac{1}{t}\left(L - \frac{2x_f}{\cos \alpha_f} - \frac{2x_d}{\cos \alpha_d} - \frac{2x_l}{\cos \alpha_l}\right).$$

We notice that $x_d$, $x_l$ and the angles $\alpha_f$, $\alpha_d$ and $\alpha_l$ are unknown until the speeds of sound in the materials are determined. This means the various equations are weakly coupled. The coupling is weak because the distances $x_d$ and $x_l$ are small in comparison with the radial distance $X_f$. The equations quickly converge if solved by an iterative scheme whereby initially the small unknowns are ignored and then increasingly refined at each iteration.

Similarly, subsequent arrivals through the lining and debris yield the speed of sound in those materials. Partial reflection of longitudinal refraction mode signals indicates the presence of a defect such as a circumferential crack whereas total reflection of the longitudinal refraction mode signals indicates the presence of a fitting such as a flange. Partial reflection of circumferential refraction mode signals indicates the presence of a defect such as a longitudinal crack. As the transducers are transported axially along the pipe, the reflection mode transducers receive a temporarily distorted signal as they pass a fitting such as a flange. Consequently both the reflection and refraction mode signals can detect corrosion, cracks and fittings. Comparison of events detected by the reflection mode signals and refraction mode signals serves to distinguish cracks from corrosion and various types of fitting, especially as the repeated use of the transducers allows a learning process to be carried out whereby the qualitative shape of reflections is used to distinguish between different features such as cracks, corrosion and fittings.

What is claimed is:

1. Apparatus for use in the characterization of a liquid-filled pipe, which apparatus comprises a vehicle capable of fitting inside the pipe and of being transported by the liquid along the pipe, the vehicle carrying rings of several ultrasonic transducers arranged such that during utilization the rings are co-axial with the pipe and spaced along the vehicle, and such that     a first ring of transducers operates in the reflection mode purely radially while     a second and a third ring of transducers operate as a pair displaced axially to each other, the pair being used in a longitudinal refraction mode in which one ring of the pair emits pulses along the pipe generally at the critical angle to the wall—that is to say, along directions spread in a cone so as to accommodate expected variations in the critical angle of the pipe, liner and debris materials—such that the wave is refracted as waves traveling within the debris, lining and pipe wall, and the other ring receives the refracted wave,     the emit ring of transducers of the refraction mode pair also has the capability of receiving reflected echoes, this being a refraction/reflection mode, and     a fourth ring of transducers is used in a circumferential refraction/reflection mode in which each transducer emits pulses in a radial plane but at the critical angle circumferentially to the wall such that the wave is refracted as a circumferential wave along the debris, lining and pipe wall and the ring then receives reflections back along the same path,     the vehicle also carrying means for measuring the distance traveled along the pipe, and a collapsible drogue to ensure that in use the flow of liquid provides sufficient drag to produce forward propulsion of the vehicle.

2. Apparatus as claimed in claim 1, wherein there are eight or more transducers equally disposed in each ring.

3. Apparatus as claimed claim 1, wherein the vehicle carries data storage means in which to save the ultrasonic information which in operation is captured at regular intervals of distance along the pipe, together with power supply means for the transducers and associated data gathering and data storage.

4. Apparatus as claimed claim 1, wherein the vehicle consists of a plurality of separate connected modules small enough to enter the pipe by means of suitable fittings.

5. Apparatus as claimed in claim 1, wherein the vehicle is neutrally buoyant, and has its center of gravity below the vehicle's geometric center.

6. Apparatus as claimed claim 1, wherein the vehicle has spacer means which in use centralize the vehicle within the pipe.

7. Apparatus as claimed in claim 6, wherein the spacer means is a plurality of springs extending laterally from the vehicle, which springs in use press gently against the pipe wall so as to centralize the vehicle.

8. Apparatus as claimed in claim 1, wherein the vehicle's distance measuring means are acoustic means, which in use involve measuring the time of travel of acoustic pulses along the pipe.

9. Apparatus for use in the characterization of a liquid-filled pipe, which apparatus comprises a vehicle capable of fitting inside the pipe and of being transported by the liquid along the pipe, the vehicle carrying rings of several ultrasonic transducers arranged such that during utilization the rings are co-axial with the pipe and spaced along the vehicle, and such that a first ring of transducers operates in the reflection mode purely radially while a second and a third ring of transducers operate as a pair displaced axially to each other, the pair being used in a longitudinal refraction mode in which one ring of the pair emits pulses along the pipe generally at the critical angle to the wall—that is to say, along directions spread in a cone so as to accommodate expected variations in the critical angle of the pipe, liner and debris materials—such that the wave is refracted as waves traveling within the debris, lining and pipe wall, and the other ring receives the refracted wave, the emit ring of transducers of the refraction mode pair also has the capability of receiving reflected echoes, this being a refraction/reflection mode, and a fourth ring of transducers is used in a circumferential refraction/reflection mode in which each transducer emits pulses in a radial plane but at the critical angle circumferentially to the wall such that the wave is refracted as a circumferential wave along the debris, lining and pipe wall and the ring then receives reflections back along the same path, the vehicle also carrying means for measuring the distance traveled along the pipe, and the vehicle is neutrally buoyant, and has its center of gravity below the vehicle's geometric center.

10. Apparatus as claimed in claim 9, wherein there are eight or more transducers equally disposed in each ring.

11. Apparatus as claimed in claim 9, wherein the vehicle carries date storage means in which to save the ultrasonic information which in operation is captured at regular intervals of distance along the pipe, together with power supply means for the transducers and associated date gathering and data storage.

12. Apparatus as claimed in claim 9, wherein the vehicle consists of a plurality of separate connected modules small enough to enter the pipe by means of suitable fittings.

13. Apparatus as claimed in claim 9, wherein the vehicle has spacer means which in use centralize the vehicle within the pipe.

14. Apparatus as claimed in claim 13, wherein the spacer means is a plurality of springs extending laterally from the vehicle, which springs in use press gently against the pipe wall so as to the pipe wall so as to centralize the vehicle.

15. Apparatus as claimed in claim 9, wherein the vehicle's distance measuring means are acoustic means, which in use involve measuring the time of travel of acoustic pulses along the pipe.

16. Apparatus for use in the characterization of a liquid-filled pipe, which apparatus comprises a vehicle capable of fitting inside the pipe and of being transported by the liquid along the pipe, the vehicle carrying rings of several ultrasonic transducers arranged such that during utilization the rings are co-axial with the pipe and spaced along the vehicle, and such that a first ring of transducers operates in the reflection mode purely radially while a second and a third ring of transducers operate as a pair displaced axially to each other, the pair being used in a longitudinal refraction mode in which one ring of the pair emits pulses along the pipe generally at the critical angle to the wall—that is to say, along directions spread in a cone so as to accommodate expected variations in the critical angle of the pipe, liner and debris materials—such that the wave is refracted as waves traveling within the debris, lining and pipe wall, and the other ring receives the refracted wave, the emit ring of transducers of the refraction mode pair also has the capability of receiving reflected echoes, this being a refraction/reflection mode, and a fourth ring of transducers is used in a circumferential refraction/reflection mode in which each transducer emits pulses in a radial plane but at the critical angle circumferentially to the wall such that the wave is refracted as a circumferential wave along the debris, lining and pipe wall and the ring then receives reflections back along the same path, the vehicle also carrying means for measuring the distance traveled along the pipe, the distance measuring means being acoustic means, which is use involve measuring the time of travel of acoustic pulses along the pipe.

17. Apparatus as claimed in claim 16, wherein there are eight or more transducers equally disposed in each ring.

18. Apparatus as claimed in claim 16, wherein the vehicle carries date storage means in which to save the ultrasonic information which in operation is captured at regular intervals of distance along the pipe, together with power supply means for the transducers and associated date gathering and data storage.

19. Apparatus as claimed in claim 16, wherein the vehicle consists of a plurality of separate connected modules small enough to enter the pipe by means of suitable fittings.

20. Apparatus as claimed in claim 16, wherein the vehicle has spacer means which in use centralize the vehicle within the pipe.

21. Apparatus as claimed in claim 16, wherein the spacer means is a plurality of springs extending laterally from the vehicle, which springs in use press gently against the pipe wall so as to centralize the vehicle.

* * * * *